United States Patent [19]

McCool

[11] Patent Number: 4,693,710
[45] Date of Patent: Sep. 15, 1987

[54] TUBE AND FITTING ASSEMBLY AND METHOD OF MAKING SAME

[75] Inventor: George W. McCool, St. Joseph, Mo.

[73] Assignee: Sherwood Medical Company, St. Louis, Mo.

[21] Appl. No.: 711,547

[22] Filed: Mar. 13, 1985

[51] Int. Cl.$^4$ ............................................. A61M 5/20
[52] U.S. Cl. ..................................... 604/283; 285/331
[58] Field of Search ............... 604/283, 280, 264, 239, 604/240, 272, 93, 164, 165; 156/73.5; 285/331, 382.2

[56] References Cited

U.S. PATENT DOCUMENTS

| | | | |
|---|---|---|---|
| 2,437,933 | 3/1948 | Brennan | 285/331 |
| 3,064,648 | 11/1962 | Bujan | 604/177 |
| 3,406,685 | 10/1968 | May | 604/164 |
| 3,515,413 | 6/1970 | Beall | 285/331 |
| 3,690,088 | 9/1972 | Anderson et al. | 156/73.5 |
| 4,239,042 | 12/1980 | Asai | 604/164 |
| 4,317,445 | 5/1982 | Robinson | 604/264 |
| 4,388,013 | 6/1983 | Bergheim et al. | 285/382.4 |
| 4,388,074 | 6/1983 | Seberg et al. | 604/177 |
| 4,391,029 | 7/1983 | Czuba et al. | 604/283 |
| 4,417,890 | 11/1983 | Dennehey et al. | 604/283 |
| 4,523,968 | 6/1985 | McCool | 604/283 |

FOREIGN PATENT DOCUMENTS

| 0001106 | 3/1979 | European Pat. Off. | 604/283 |
|---|---|---|---|
| 2907832 | 9/1980 | Fed. Rep. of Germany | 604/283 |

Primary Examiner—Stephen C. Pellegrino
Attorney, Agent, or Firm—Stanley N. Garber; Andrew J. Beck; William R. O'Meara

[57] ABSTRACT

A tube and fitting assembly is disclosed which includes a plastic fitting with a hollow pin frictionally receiving an end portion of a plastic tube, and an integral collar surrounding the pin and tube end portion and with the tube end portion clamped between the pin and collar. A method of making a tube and fitting assembly is disclosed which includes spin-forming the collar of a fitting about an end portion of a plastic tube while the end portion is disposed on a hollow pin concentric with the collar.

12 Claims, 6 Drawing Figures

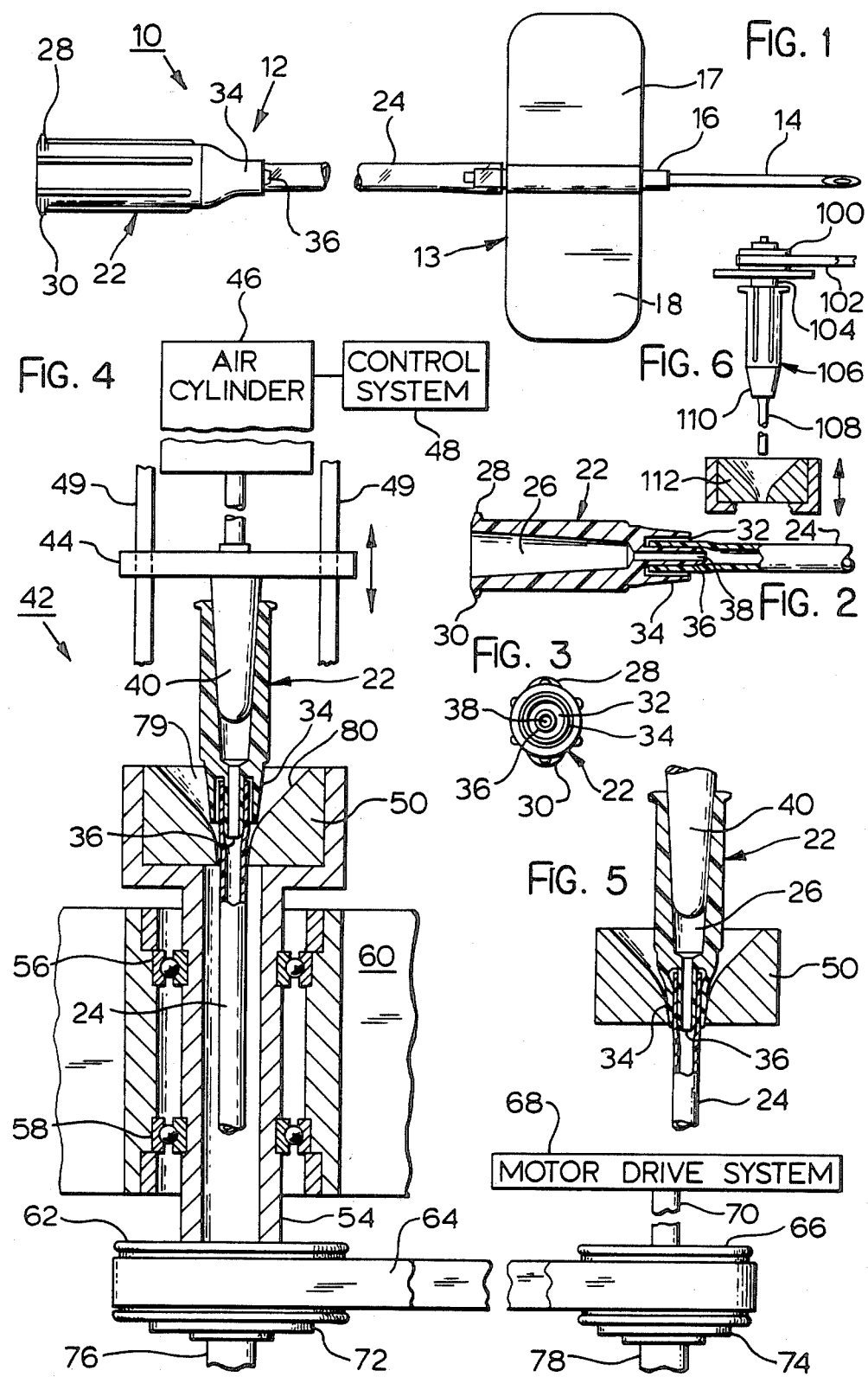

TUBE AND FITTING ASSEMBLY AND METHOD OF MAKING SAME

DESCRIPTION

1. Technical Field

This invention relates to tube and fitting assemblies and, more particularly, to an improved tube and fitting assembly and to an improved method of making a tube and fitting assembly.

2. Background Art

Medical tube assemblies such as employed in or used as catheters, fluid transfer tubes and the like, generally use a tube fitting with a luer connector at one end for connecting the tube or catheter to another fluid device in a fluid system.

The tube and fitting obviously should be so connected together that they do not separate or result in fluid leakage under mechanical pulling forces and fluid pressures that may be encountered when the assembly is in use. However, such failures have been encountered, especially when the tube and fitting are of a relatively small size.

One method of connecting the tube and fitting together is to provide the fitting with a recess or bore and solvent bond the outer surface of one end of the tube to the walls of the recess. With such an assembly, however, any separating forces or pulling force on the catheter encountered when in use tends to narrow the catheter, resulting in inward forces tending to pull the catheter inwardly away from the recess walls. Such connections have not been entirely satisfactory, especially where the tube is of small diameter. Also, the solvent generally weakens the catheter and fitting at the connection. Furthermore, with such a method the inner diameter of the recess and the outer diameter of the tube must be held to close tolerances, further complicating the manufacture of such an assembly.

Another method employed is to bond the inner surface of one end portion of a tube to the outer surface of a hollow pin. With this method, the solvent tends to weaken the walls of both the pin and the tube, resulting in a weak connection between the fitting and tube, especially where the tube and pin are of relatively small diameters and the wall thicknesses of the pin and tube are small.

The use of solvents and adhesives in obtaining a fluid-tight connection between a tube and fitting also has the disadvantages of producing fumes and odors, and such materials are not easily employed and must be stored.

SUMMARY OF THE INVENTION

It is therefore an object of the present invention to provide an improved tube and fitting assembly, and method of making the same, which overcome one or more of the above problems.

Another object of the invention is to provide an improved method of connecting a plastic tube and plastic fitting to obtain a strong, fluid-tight connection between the tube and fitting and without the need of solvents or adhesives.

In accordance with one aspect of the present invention, a method of making a tube and fitting assembly is disclosed which includes the steps of providing a plastic fitting having an end socket and a hollow pin extending concentrically within the socket, and inserting one end portion of a tube into the socket and onto the pin. A die is provided having a die-forming cavity narrowing toward one end. While effecting relative rotation and axial movement of the tube and fitting, the fitting moves into the die-forming cavity and is urged in a direction toward the narrow end so that the outer surface of the walls of the socket engage the walls of the opening and are inwardly formed against the outer surface of the end portion of the tube to thereby compress the end portion of the tube.

In accordance with another aspect of the present invention, a tube and fitting assembly is provided which includes a fitting with an socket, a hollow pin extending concentrically in the socket, and a tube having an end portion disposed over the pin within the socket, the end portion of the tube being clamped between the inner surface of the socket wall and the outer surface of the pin to form a fluid-tight connection between the fitting and tube.

These, as well as other objects and advantages of the invention, will become apparent from the following detailed description and accompanying drawing.

BRIEF DESCRIPTION OF THE DRAWING

FIG. 1 is an elevational view of an infusion catheter made in accordance with the present invention;

FIG. 2 is a longitudinal cross-sectional view of the fitting and tube of FIG. 1 but before they are permanently secured together;

FIG. 3 is an end view of the fitting of FIG. 2 without the tube;

FIG. 4 is a cross-sectional view illustrating apparatus used in the method of permanently connecting the fitting and tube of FIG. 2 together; and FIG. 5 is a cross-sectional view of a portion of the apparatus of FIG. 4 illustrating another step in the method of permanently connecting the fitting and tube of FIG. 1 together.

FIG. 6 is a view illustrating an alternative embodiment for connecting the fitting and tube of FIG. 2 together.

DETAILED DESCRIPTION OF THE PREFERRED EMBODIMENT AND METHOD OF MAKING THE SAME

Referring now to the drawings, there is shown in FIG. 1 an infusion or intravenous catheter 10 including a fitting and tube assembly 12 made in accordance with the present invention, connected to a needle assembly 13 which includes an intravenous hollow metal needle or cannula 14 having a needle hub 16 that is shown having a pair of oppositely extending, flat wings 17 18 integrally connected to the hub 16. The hub surrounds and is fixed to the needle 14. The hub and wings may be made of a suitable plastic such as polyvinyl chloride. The assembly 12 includes a fitting or connector 22 fixed to one end portion of a tube 24. The other end of tube 24 is connected to the proximal end of the needle hub 16 in fluid communication with needle 14. In use, the needle 14 is inserted into the vein of a patient and the wings 17 and 18 are secured such as by taping them to the skin of a patient to maintain the needle cannula in the desired position. A source of infusion liquid can be connected to the fitting 22 so that infusion liquid flows through tube 24 and needle 14 to the vein of a patient. While the fitting and tube assembly 12 is shown connected to form an intravenous catheter 10, the assembly 12 may be connected to form other apparatus such as associated with other types of catheters for purposes other than the infusion of liquid into the vein of a patient.

The fitting 22 is shown in its original condition in FIG. 2, that is, in its molded condition before being permanently attached to the tube 24. As seen in FIG. 2, the fitting 22 has a conventional luer tapered bore 26 and a pair of dimetrically opposed luer lock ears or thread members 28 and 30 at the left or proximal end of the fitting. The tapered bore 26 and ears 28 are adpated to be connected with a conventional male luer lock connector of another device such as a luer lock connector of a tube connected to an infusion liquid source. As also seen in FIG. 3, fitting 22 has an annular recess or socket 32 having an annular socket wall or collar 34 at the opposite or distal end of the fitting. A concentric, hollow pin 36 extends axially and centrally of the socket 32 and is shown extending externally of the distal end of the socket wall 34. Pin 36 has a bore 38 which connects with the luer tapered bore 26. The proximal end potion of tube 24 is inserted into socket 32 over pin 36. Preferably, the outer diameter of the pin 36 and the inner diameter of tube 24 are formed such that the tube forms a snug or tight friction fit with the outer surface of the pin. Generally, this step of inserting the tube 24 into the socket 32 of the fitting 22 is performed before the other or distal end of tube 24 is connected to the needle assembly 13 or any other device.

Fitting 22 is a unitary member, preferably molded of a thermoplastic material, preferably a polypropylene plastic, although other plastics such as polyethylene, polyvinyl chloride or others may be used in some cases. Plastic tube 24 may be made out of a suitable plastic, for example, it may be extruded from polyvinyl chloride, although it may be made of rubber or from other plastics such as polyethylene or urethane. As used herein, the term "plastic tube" is intended to mean a tube made of a material such as synthetic rubber or plastic elastomeric material.

After the tube 24 has been inserted into the socket 32 of the fitting 22 as shown in FIG. 2, the fitting is inserted onto a luer tapered pin 40 of a spin-forming mechanism 42 shown for illustration in FIG. 4, and which is employed in the process of permanently fixing the fitting 22 in fluid-tight, fixed connection with the tube 24. The mechanism pin 40 is connected to a plate 44 which is schematically illustrated as being driven up and down on guide rails 49 by an air cylinder 46 automatically operated by a cylinder control system 48. Since the tube 24 is in snug, frictional fitting relation with the pin 36 of the fitting, the two remain together and can be handled manually or by mechanical apparatus before being permanently fixed together without the two separating.

The fitting and tube are shown in FIG. 4 extending into a spin-forming die indicated generally at 50 which is mounted in fixed relation in the upper end of a driven shaft 54 mounted for rotation in bearings 56 and 58 in a stationary housing 60. Shaft 54 is connected to a pulley 62 which is driven by a pulley belt 64 that is, in turn, driven by a pulley 66. Pulley 66 is illustrated as being driven by a motordrive system 68 through a shaft 70. The pulleys 62 and 66 may be mounted for rotation by pulley bearings 72 and 74, respectively, that are mounted on stationary shafts 76 and 78, respectively.

The spin-forming die 50 has a die-forming cavity 79 with a forming surface 80 which smoothly tapers radially inwardly and downwardly to a narrow end at the bottom of the die so that the surface is generally frusto-conical in shape. The die cavity 79 is open at the top and bottom so that the tube 24 can pass through the die during spin-forming operations. Die 50 is of a metal such as a stainless steel and with the surface 80 polished.

By moving the fitting 22 with the tube 24 connected to the pin 36 of the fitting into the die 50 (FIG. 4) with a downward force, such as under the force applied by cylinder 46 to pin 40, the socket walls or collar 34 of the fitting engage the rotating walls or surface 80 of die cavity 79 and move toward the narrow end of the cavity. With the downward force applied to the pin 40 and fitting 22, the collar 34 of the fitting 22 moves further into the narrowing lower portion of the die cavity 79 with the walls of collar 34 narrowing or becoming reduced in diameter. As fitting 22 moves further into the die 50, the collar 34 becomes slightly extruded longitudinally or distally and is tightly clamped against the outer surface of the end of tube 24 as shown in FIG. 5. The heat generated by the frictional engagement between the collar 34 and the rotating cavity 79 heats the collar and contributes to the process of forming the collar about the tube 24. The fitting 22 is now moved upwardly and out of the die 50 such as by pin 40 and the action of air cylinder 46. The fitting 22 and the attached tube 24 are removed from pin 40 and entirely removed from the die mechanism 42 with the fitting and tube assembly in its permanently shaped condition shown in FIG. 5. The end portion of tube 24 is tightly clamped between the inner surface of collar 34 and the outer surface of pin 36, as seen in FIG. 5, so that a fluid-tight, mechanically strong connection is made between the fitting 22 and tube 24.

The distal end of the tube 24 may then be connected to the proximal end of the needle hub 16 where the fitting and tube assembly is to be used in the infusion catheter of FIG. 1.

In this way, the fitting and tube assembly 12 can be used in relatively high fluid pressure systems without resulting in a leak at the connection between the fitting and tube or separation of that. Successful fitting and tube assemblies were made which employed a fitting molded of a polypropylene plastic in the shape of fitting 22. The inside diameter of the collar 34 was about 3.76 millimeters (mm); the outside diameter at the distal end of the socket was about 4.52 mm; the outside diameter of pin 36 was about 1.778 mm; and the diameter of the pin bore 38 was about 0.965 mm. The pin 36 had an axial length measured from the bottom of the socket of about 5.84 mm and extended outwardly about 1.52 mm from the free end of the socket wall 34. The radial dimension between the inner surface of wall 34 and the outer surface of pin 36 was about 0.991 mm. The plastic tube was extruded from polyvinyl chloride and had inner and outer diameters of about 1.34 mm and 2.18 mm, respectively, so that the radial thickness of the tube side wall was about 0.42 mmm. The finished fitting and tube assembly was tested under a pressure of 45 psi without leakage.

The spin-forming die used to make those assemblies was similar in shape to die 50. The die was rotated at a speed of 2550 rpm, a force of about 24 lbs. was applied to the fitting during insertion into the die, and the time of forming was about 1 second. While specific materials for the tube and fitting, specific die speed, applied force, and forming time have been mentioned herein for purposes of illustration, it will be apparent to those skilled in the art that variations in the above can be made and good fitting and tube assemblies obtained. For example, the die speed, in some cases, may be a speed between 1000 and 3000 rpm. Also, in some cases, the force applied on the fitting during forming may be, for example, between 20 and 30 lbs. Also, this method of making tube and fitting assemblies is especially important where the tubes are of relatively small size, for example, tubes having outer diameters below about 6.25 mm.

No solvent or adhesive is required to secure the fitting and tube together in the present spin-forming method. This, of course, avoids the disadvantages of applying such a solvent or adhesive, storing it, and the undesirable gases and smells that result from the use of solvents or adhesives. Tube and fitting assemblies spin-formed as discussed above provide a strong assembly that can withstand relatively high forces tending to pull the fitting and tube apart.

FIG. 6 illustrates a method of making a tube and fitting assembly in which the fitting and tube are rotated while the die is not rotated. As seen in FIG. 6, a pulley 100, driven by a pulley belt 102, rotates a pin 104 carrying a fitting 106 similar to fitting 22 in shape. A tube 108 having one end portion disposed on the hollow pin (not shown) of the fitting extends into an end collar 110 of the fitting. A forming die 112 is illustrated as being movable up and down as indicated by the arrows adjacent the die. In this case, the die moves upwardly onto the rotating collar 110 of the fitting causing the collar to be spin-formed about the upper end of tube 108 to provide a finished assembly with the tube clamped between the formed collar 110 and pin 104. The finished assembly in this case is similar to that shown in FIG. 5 in connection with assembly 12.

It will now be apparent that the various objects and advantages of the present invention have been met. As various changes may be made in the above construction and method of making the construction without departing from the scope of the invention, it is intended that all matter contained in the above description or shown in the accompanying drawing shall be interpreted as illustrative and not in a limiting sense.

I claim:

1. A medical tube and fitting assembly comprising a molded single-piece thermoplastic fitting including a luer connector having a luer tapered bore for connection with a luer tapered connector of another member, an axially extending pin adjacent one end of said fitting having a bore connected with said luer tapered bore and of smaller diameter than that of said luer tapered bore, a collar surrounding said pin and being open at the distal end thereof, said luer connector, said collar and said pin all being of the same thermoplastic material and integrally and jointlessly connected together, a plastic tube having one end portion disposed in said collar and surrounding said pin in tight, frictional engagement therewith and extending distally beyond the distal end of the said collar, said collar being heat and pressure shaped by spin forming into surrounding, tight, frictional engagement with the radially outer surface of said tube end portion with said tube end portion clamped between the radially inner surface of said collar and the radially outer surface of said pin to fixedly connect said collar, pin and tube together to form a fluid-tight mechanical connection between said fitting and said tube, said mechanical connection being established solely by said collar, pin and tube during said spin forming, the outer wall of said collar tapering distally inwardly and being of substantially minimum outer diameter at the distal end thereof.

2. The assembly of claim 1 wherein said pin extends substantially to the distal end of said collar.

3. The assembly of claim 1 wherein said fitting is formed of a polypropylene plastic.

4. The assembly of claim 1 wherein said collar is in tight frictional engagement with the outer surface of said tube end portion with said tube end portion clamped between the major portion of the radially inner surface of said collar and the major portion of the radially outer surface of said pin.

5. The assembly of claim 4 wherein said pin extends substantially distally to the distal end of said collar.

6. The assembly of claim 4 wherein said tube is clamped between said pin and said collar at the distal end of said collar.

7. The assembly of claim 5 wherein said pin extends distally beyond the distal end of said collar.

8. An infusion catheter for supplying an infusion liquid to the vein of a patient comprising a unitary thermoplastic fitting including an axially extending pin adjacent one end thereof having a bore therethrough, a collar surrounding said pin in concentric spaced relation thereto and being open at the distal end thereof, and a luer connector having a luer tapered bore open at the proximal end of said fitting and connected in fluid communication with said pin bore, said pin bore being of smaller diameter than that of said luer tapered bore, said pin, said collar and said luer connector all being of the same thermoplastic material and integrally formed together as a jointless, molded member, a plastic catheter having a proximal end portion surrounding said pin in tight-fitting relation within said collar, said collar being heat and pressure shaped by spin forming into tight-fitting relation with the outer surface of said catheter end portion so that said catheter end portion is clamped in fluid-tight relation between the major portions of the outer and inner surfaces of said pin and collar respectively, to fixedly connect said collar, pin and catheter together to form a fluid-tight mechanical connection between said fitting and said catheter, said mechanical connection being established solely by said collar, pin and tube during said spin forming, the outer wall of said collar tapering distally inwardly and being of substantially minimum outer diameter at the distal end thereof, and an intravenous needle cannula connected to the distal end portion of said catheter for insertion into the vein of a patient.

9. The catheter of claim 8 further including a plastic needle hub spaced distally of said fitting and connected to and surrounding said needle cannula and having opposed wings connected thereto for connecting said needle cannula to a patient.

10. The catheter of claim 8 wherein said pin extends substantially to the distal end of said collar.

11. The catheter of claim 10 wherein said fitting is of a polypropylene.

12. The assembly of claim 8 wherein said pin extends distally substantially to the distal end of said collar.

* * * * *